(12) United States Patent
Honda et al.

(10) Patent No.: US 10,377,703 B2
(45) Date of Patent: Aug. 13, 2019

(54) METHOD FOR PRODUCING 4-(TRIFLUOROMETHYLSULFONYL)PHENOL COMPOUND

(71) Applicant: SUMITOMO CHEMICAL COMPANY, LIMITED, Tokyo (JP)

(72) Inventors: Yuta Honda, Osaka (JP); Yohei Tanaka, Osaka (JP); Kazuya Ueki, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/737,492

(22) PCT Filed: Jul. 19, 2016

(86) PCT No.: PCT/JP2016/071117
§ 371 (c)(1),
(2) Date: Dec. 18, 2017

(87) PCT Pub. No.: WO2017/014214
PCT Pub. Date: Jan. 26, 2017

(65) Prior Publication Data
US 2018/0186732 A1    Jul. 5, 2018

(30) Foreign Application Priority Data

Jul. 21, 2015 (JP) ................................. 2015-143694

(51) Int. Cl.
C07C 315/02    (2006.01)
C07C 315/04    (2006.01)
C07C 317/22    (2006.01)
C07C 317/36    (2006.01)
C07C 209/36    (2006.01)
(Continued)

(52) U.S. Cl.
CPC .......... *C07C 315/02* (2013.01); *C07C 201/08* (2013.01); *C07C 209/36* (2013.01); *C07C 315/04* (2013.01); *C07C 317/22* (2013.01); *C07C 317/36* (2013.01); *C07C 53/128* (2013.01); *C07C 2523/42* (2013.01)

(58) Field of Classification Search
None
See application file for complete search history.

(56) References Cited

U.S. PATENT DOCUMENTS 5,028,711 A    7/1991  Stenzel et al.
6,040,450 A    3/2000  Davies et al.
(Continued)

FOREIGN PATENT DOCUMENTS

CA    2102904 A1    11/1992
JP    2-72171 A    3/1990
(Continued)

OTHER PUBLICATIONS

International Search Report, issued in PCT/JP2016/071117, PCT/ISA/210, dated Sep. 20, 2016.
(Continued)

*Primary Examiner* — Rosalynd A Keys
(74) *Attorney, Agent, or Firm* — Birch, Stewart, Kolasch & Birch, LLP

(57) ABSTRACT

A compound represented by formula (4):

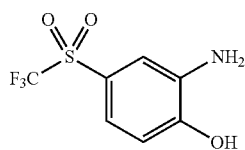

(4)

can be produced by adding a heterogeneous transition metal catalyst to a solution containing a compound represented by formula (3):

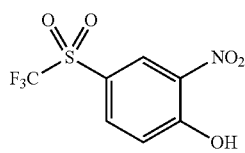

(3)

obtained by performing a nitration reaction by adding a nitrating agent to a solution containing a compound represented by formula (2):

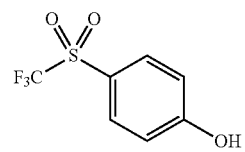

(2)

obtained by oxidizing a compound represented by formula (1):

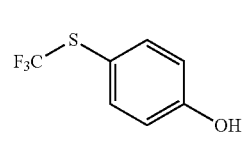

(1)

(Continued)

with hydrogen peroxide in the presence of sodium tungstate and a saturated C8 carboxylic acid, then adding water to the resultant mixture, and separating the resultant solution.

5 Claims, No Drawings

(51) Int. Cl.
  *C07C 201/08* (2006.01)
  *C07C 53/128* (2006.01)

(56) References Cited

U.S. PATENT DOCUMENTS

| | | | | |
|---|---|---|---|---|
| 8,524,766 | B2* | 9/2013 | Sonesson | C07D 311/20 |
| | | | | 514/452 |
| 9,615,580 | B2* | 4/2017 | Takahashi | C07D 263/57 |
| 2011/0105461 | A1 | 5/2011 | Sonesson et al. | |
| 2012/0253054 | A1* | 10/2012 | Yasumura | C07D 341/00 |
| | | | | 549/11 |
| 2013/0274501 | A1 | 10/2013 | Shrawat et al. | |
| 2014/0170855 | A1 | 6/2014 | Nakajima et al. | |
| 2015/0313234 | A1 | 11/2015 | Takahashi et al. | |
| 2017/0137377 | A1 | 5/2017 | Ueki et al. | |

FOREIGN PATENT DOCUMENTS

| | | |
|---|---|---|
| JP | 6-508109 A | 9/1994 |
| JP | 2001-517654 A | 10/2001 |
| JP | 2010-208990 A | 9/2010 |
| JP | 2015-59100 A | 3/2015 |
| WO | WO 2013/022099 A1 | 2/2013 |
| WO | WO 2014/104407 A1 | 7/2014 |
| WO | WO 2015/198850 A1 | 12/2015 |

OTHER PUBLICATIONS

International Preliminary Report on Patentability and an English Translation of the Written Opinion of the International Searching Authority (Forms PCT/IB/326, PCT/IB/373, and PCT/ISA/237), dated Feb. 1, 2018, for International Application No. PCT/JP2016/071117.

* cited by examiner

METHOD FOR PRODUCING 4-(TRIFLUOROMETHYLSULFONYL)PHENOL COMPOUND

TECHNICAL FIELD

The present invention relates to a method for producing 4-(trifluoromethylsulfonyl)phenol, 4-(trifluoromethylsulfonyl)-2-nitrophenol, and 4-(trifluoromethylsulfonyl)-2-aminophenol.

BACKGROUND ART 4-(Trifluoromethylsulfonyl)phenol, 4-(trifluoromethylsulfonyl)-2-nitrophenol and 4-(trifluoromethylsulfonyl)-2-aminophenol are useful as production intermediates of pharmaceuticals and agrochemicals (see, for example, WO2014/104407).

A method for producing 4-(trifluoromethylsulfonyl)phenol by oxidizing 4-(trifluoromethylsulfanyl)phenol with sodium tungstate and hydrogen peroxide in acetic acid is known, for example, in WO2009/133107.

SUMMARY OF THE INVENTION

On the other hand, the present invention provides a novel method for producing 4-(trifluoromethylsulfonyl)phenol. The present invention also provides a method for producing 4-(trifluoromethylsulfonyl)-2-nitrophenol and 4-(trifluoromethylsulfonyl)-2-aminophenol.

According to the present invention, a compound represented by formula (2):

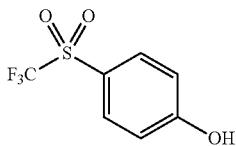

(2)

(hereinafter referred to as Compound (2)) can be produced by oxidizing a compound represented by formula (1):

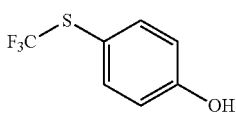

(1)

(hereinafter referred to as Compound (1)) with hydrogen peroxide in the presence of sodium tungstate and a saturated C8 carboxylic acid.

Further, a compound represented by formula (3):

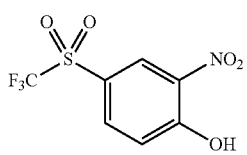

(3)

(hereinafter referred to as Compound (3)) can be produced by adding a nitrating agent to a solution containing Compound (2) obtained by oxidizing Compound (1) with hydrogen peroxide in the presence of sodium tungstate and a saturated C8 carboxylic acid, then adding water to the resultant mixture, and separating the resultant solution.

Furthermore, a compound represented by formula (4):

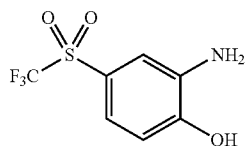

(4)

(hereinafter referred to as Compound (4)) can be produced by performing a reduction reaction by adding a heterogeneous transition metal catalyst to a solution containing Compound (3) obtained by performing a nitration reaction by adding a nitrating agent to a solution containing Compound (2) obtained by oxidizing Compound (1) with hydrogen peroxide in the presence of sodium tungstate and a saturated C8 carboxylic acid, then adding water to the resultant mixture, and separating the resultant solution.

MODE FOR CARRYING OUT THE INVENTION

First, a method for producing Compound (2) by oxidizing Compound (1) with hydrogen peroxide in the presence of sodium tungstate and a saturated C8 carboxylic acid will be explained.

The amount of the saturated C8 carboxylic acid used is usually 0.1 to 5.0 times by weight and preferably 0.5 to 2.0 times by weight of Compound (1).

A hydrate such as a dihydrate may be used for sodium tungstate. The amount of sodium tungstate used is usually 0.001 to 0.1 mol and preferably 0.01 to 0.1 mol, based on 1 mol of Compound (1).

Hydrogen peroxide is usually used in an aqueous solution, and its concentration is usually 10 to 70% by weight and preferably 30 to 60% by weight.

The amount of hydrogen peroxide used is usually 1.8 to 5 mol, preferably 2.0 to 3.5 mol, and more preferably 2.4 to 3.0 mol, based on 1 mol of Compound (1).

The reaction temperature is in the range of 50 to 100° C. and preferably 60 to 80° C.

The reaction time is usually 1 to 50 hours.

From the viewpoint of safety, it is preferable to add hydrogen peroxide at the end, in the mixing order of Compound (1), sodium tungstate, the saturated C8 carboxylic acid, and hydrogen peroxide.

A commercially available product can be used as it is for Compound (1), but a commercially available product often contains a fluoride which adversely affects a reaction container, so it is preferable to wash Compound (1) with alkaline water such as a 1% by weight aqueous sodium hydroxide solution in advance.

Specific examples of the saturated C8 carboxylic acid include 2-ethylhexanoic acid, octanoic acid, 6-methylheptanoic acid and 2-propylpentanoic acid, and 2-ethylhexanoic acid is preferable.

The reaction solvent is not essential in this oxidation reaction, but an inert solvent, for example, nitriles such as acetonitrile and propionitrile; aromatic hydrocarbons such as toluene, xylene and ethylbenzene; and sulfolane may be used. In producing Compound (3) or Compound (4), it is advantageous to use a saturated C8 carboxylic acid or a saturated C8 carboxylic acid and water as a reaction solvent, in carrying out the nitration reaction and the reduction reaction following the oxidation reaction, without isolating Compound (2) or Compound (3).

After completion of the reaction, for example, water, an aqueous sodium sulfite solution, an aqueous sodium bisulfite solution, an aqueous sodium thiosulfate solution or the like is added to the reaction mixture, and if necessary, a hydrophobic organic solvent is added and the organic layer is separated to obtain a solution containing Compound (2). A solvent such as hexane is added to the obtained organic layer to precipitate a solid, and the precipitated solid is filtered, whereby Compound (2) can be isolated. The isolated Compound (2) can also be further purified by recrystallization or chromatography.

Also, in the case of producing Compound (3) or Compound (4), the solution containing Compound (2) may be directly used in the next step without isolating Compound (2).

Next, a method for producing Compound (3) by adding a nitrating agent to the solution containing Compound (2) obtained by oxidizing Compound (1) with hydrogen peroxide in the presence of sodium tungstate and a saturated C8 carboxylic acid, then adding water to the resultant mixture, and separating the resultant solution will be explained.

The method of obtaining the solution containing Compound (2) from Compound (1) is as described above.

Compound (3) can be produced by adding a nitrating agent to the solution containing Compound (2). A nitrating agent may be added after concentrating the solution containing Compound (2).

In the nitration reaction, a solvent may be added to the solution containing Compound (2). Examples of the solvent include ethers such as diethyl ether, tetrahydrofuran and methyl tert-butyl ether; nitriles such as acetonitrile and propionitrile; saturated C1-6 carboxylic acids; and sulfolane.

Nitric acid is usually used as a nitrating agent. Generally, a 60 to 98% by weight of $HNO_3$ aqueous solution or fuming nitric acid is used for nitric acid.

The amount of nitric acid used is usually from 1.0 to 1.5 mol and preferably from 1.1 to 1.3 mol, based on 1 mol of Compound (1), with respect to the amount of $HNO_3$.

Further, the nitration reaction is usually carried out in the presence of sulfuric acid. Concentrated sulfuric acid (90% or more by weight of a $H_2SO_4$ aqueous solution) is generally used for sulfuric acid.

The amount of the sulfuric acid used is usually 0.1 to 20 times by weight and preferably 0.5 to 5 times by weight of Compound (1).

In the nitration reaction, for example, sulfuric acid is added to the solution containing Compound (2), and then nitric acid is added.

The reaction temperature is usually in the range of 0 to 100° C. and preferably 5 to 50° C.

The reaction time is usually 1 to 50 hours.

After completion of the reaction, for example, water is added to the reaction mixture, and if necessary, a hydrophobic organic solvent is added and the organic layer is separated to obtain a solution containing Compound (3). A solvent such as hexane is added to the obtained organic layer to precipitate a solid, and the precipitated solid is filtered, whereby Compound (3) can be isolated. The isolated Compound (3) can also be further purified by recrystallization or chromatography.

In the case of producing Compound (4), the solution containing Compound (3) may be directly used in the next step without isolating Compound (3).

Next, a method for producing Compound (4) will be explained, said method is performed by oxidizing Compound (1) with hydrogen peroxide in the presence of sodium tungstate and a saturated C8 carboxylic acid, then adding water to the resultant mixture, and separating the resultant solution containing Compound (2), by adding a nitrating agent to the obtained solution and separating the resultant solution containing Compound (3), and performing a reduction reaction by adding a heterogeneous transition metal catalyst to the obtained solution.

The method of obtaining the solution containing Compound (2) from Compound (1) and further obtaining the solution containing Compound (3) is as described above.

Compound (4) can be produced by adding a heterogeneous transition metal catalyst to a solution containing Compound (3) and performing a reduction reaction.

The heterogeneous transition metal catalyst is a Raney catalyst such as Raney nickel or Raney cobalt and a heterogeneous platinum group catalyst such as palladium/carbon, palladium/silica, palladium/alumina, platinum/carbon, platinum/silica, platinum/alumina, rhodium/carbon, rhodium/silica, rhodium/alumina, iridium/carbon, iridium/silica or iridium/alumina.

A heterogeneous platinum catalyst, that is, a heterogeneous platinum group catalyst of palladium, platinum, ruthenium, rhodium, iridium or osmium that is a platinum group element is preferable, and platinum/carbon and palladium/carbon are more preferable in an industrial production method.

The amount of the heterogeneous transition metal catalyst used is usually 0.0001 to 0.05 mol and preferably 0.0003 to 0.01 mol, based on 1 mol of Compound (1).

Further, in addition to the heterogeneous transition metal catalyst, a vanadium compound may be used as a co-catalyst. Examples of the vanadium compound used in the reaction include vanadium alone, inorganic vanadium compounds, organic complexes with oxalate or acetylacetonate, and the like.

Inorganic salts, oxo salts and hydrates thereof whose oxidation state is 0, II, III, IV or V and vanadium(V) oxide are preferable, vanadate(V) or hydrates of vanadate(V) are more preferable, and ammonium vanadate (V) is particularly preferable.

In the reduction reaction, a solvent may be added to the solution containing Compound (3). Examples of the solvent include alcohols such as methanol, ethanol, 1-propanol, 2-propanol and 1-butanol; aromatic hydrocarbons such as toluene, xylene and ethylbenzene; aliphatic hydrocarbons such as hexane and heptane; aliphatic halogenated hydrocarbons such as dichloromethane and 1,2-dichloroethane; ethers such as diethyl ether, tetrahydrofuran and methyl tert-butyl ether; esters such as ethyl acetate and butyl acetate; C6 to C10 aliphatic carboxylic acids; and water.

The reduction reaction is carried out under a hydrogen atmosphere. The hydrogen partial pressure of the reaction is usually 0.01 to 5 MPa and preferably 0.05 to 1 MPa.

The reaction temperature is in the range of usually 0 to 100° C. and preferably 10 to 50° C.

The reaction time is usually 1 to 50 hours.

After completion of the reaction, the heterogeneous transition metal catalyst is removed by filtration, and the obtained filtrate is concentrated, crystallized, and the like, whereby Compound (4) can be isolated. In the crystallization, seed crystals may be added to the solution containing Compound (4) to precipitate crystals, followed by cooling, and the obtained crystals may be filtered. The isolated compound (4) can also be further purified by recrystallization or chromatography.

EXAMPLES

Hereinafter, the present invention will be more specifically explained with reference to examples. In the following examples, the contents are all values obtained by HPLC under the following measurement conditions.

Detector: Ultraviolet absorption photometer (measurement wavelength: 250 nm)
Column: SUMIPAX ODS Z-CLUE manufactured by Sumika Chemical Analysis Service, Ltd. (3 μm, 4.6 mm I.D.×100 mm)
Column temperature: constant temperature around 40° C.
Mobile phase A: 0.1% aqueous phosphoric acid solution
Mobile phase B: acetonitrile
Gradient condition: The concentration gradient is controlled by changing the mixing ratio of mobile phase B as follows.

| Time (min) | Mobile phase B (%) |
|---|---|
| 0 | 10 |
| 40 | 90 |
| 50 | 90 |
| 50.1 | 10 |
| 60 | 10 |

Example 1

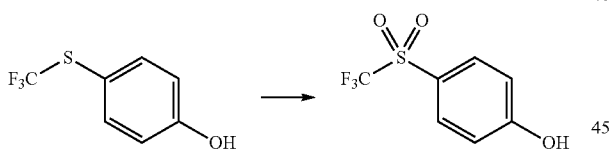

To a mixture of 20.0 g of 4-(trifluoromethylsulfanyl)phenol, 10.0 g of water, 10.0 g of 2-ethylhexanoic acid and 1.70 g of sodium tungstate dihydrate, 30.03 g of 35% by weight of aqueous hydrogen peroxide was added dropwise at 75° C. over 10.5 hours, and the mixture was stirred for 12 hours. A 22% by weight of aqueous sodium sulfite solution was added dropwise to the reaction mixture, and the layers were separated. The obtained aqueous layer was extracted with 10.0 g of 2-ethylhexanoic acid. The two obtained organic layers were combined to obtain 42.65 g (content: 53.0% by weight) of a solution containing 4-(trifluoromethylsulfonyl)phenol.

To the obtained solution, 80.0 g of hexane was added and the solution was cooled to 0° C. and kept at this temperature for 3 hours to precipitate crystals. The precipitated crystals were filtered, and washed sequentially with water and xylene, and the obtained crystals were dried under reduced pressure to obtain 19.16 g of 4-(trifluoromethylsulfonyl)phenol (content: 98.1% by weight).

Example 2

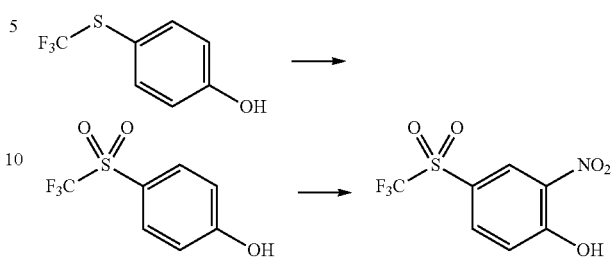

To a mixture of 75.0 g of 4-(trifluoromethylsulfanyl)phenol, 37.5 g of water, 37.5 g of 2-ethylhexanoic acid and 6.38 g of sodium tungstate dihydrate, 112.60 g of 35% by weight of aqueous hydrogen peroxide was added dropwise at 75° C. over 10.5 hours, and the mixture was stirred for 12 hours. A 22% by weight of aqueous sodium sulfite solution was added dropwise to the reaction mixture, and the layers were separated. The obtained aqueous layer was extracted with 37.5 g of 2-ethylhexanoic acid. The two obtained organic layers were combined, 7.5 g of water was added thereto, then 214.63 g of 96% by weight of sulfuric acid was added dropwise thereto, and 28.79 g of 98% by weight of nitric acid was further added dropwise thereto at 30° C. over 5 hours. After stirring for 1 hour, the reaction mixture was brought to room temperature, 29.27 g of water was added thereto, followed by adding dropwise 120.01 g of a 28% by weight of aqueous sodium hydroxide solution, and the solution was separated. To the obtained organic layer, 73.18 g of water was added and the layers were separated to obtain 187.16 g (content: 52.0% by weight) of a solution containing 4-(trifluoromethylsulfonyl)-2-nitrophenol.

To the obtained solution, 150.0 g of hexane was added and the solution was cooled to 0° C. and kept at this temperature for 3 hours to precipitate crystals. The precipitated crystals were filtered, and washed sequentially with water and hexane, and the obtained crystals were dried under reduced pressure to obtain 79.04 g of 4-(trifluoromethylsulfonyl)-2-nitrophenol (content: 98.5% by weight).

Example 3

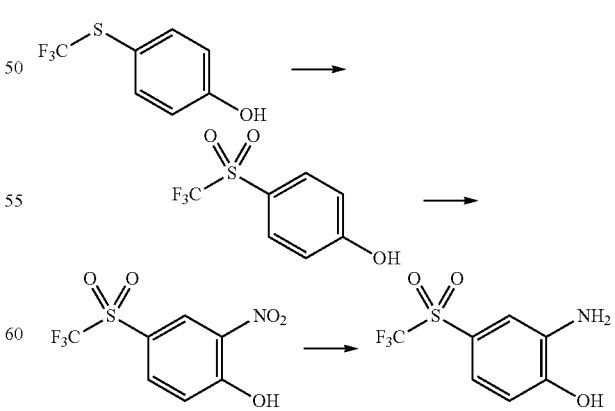

To a mixture of 80.0 g of 4-(trifluoromethylsulfanyl)phenol, 40.0 g of water, 40.0 g of 2-ethylhexanoic acid and 6.80 g of sodium tungstate dihydrate, 120.11 g of 35% by weight of aqueous hydrogen peroxide was added dropwise at 75° C. over 10.5 hours, and the mixture was stirred for 12 hours. A 22% by weight of aqueous sodium sulfite solution was added dropwise to the reaction mixture, and the layers were separated. The obtained aqueous layer was extracted with 40.0 g of 2-ethylhexanoic acid. The two resulting organic layers were combined.

To 198.19 g of the obtained organic layer, 8.0 g of water was added, followed by adding dropwise 228.94 g of 96% by weight of sulfuric acid, and further adding dropwise 30.71 g of 98% by weight of nitric acid at 30° C. over 5 hours. After stirring for 1 hour, the reaction mixture was brought to room temperature, 31.23 g of water was added thereto, followed by adding dropwise 128.05 g of a 28% by weight of aqueous sodium hydroxide solution, and the layers were separated. To the obtained organic layer, 78.06 g of water was added and the solution was separated to obtain 237.48 g (content: 41.6% by weight) of a solution containing 4-(trifluoromethylsulfonyl)-2-nitrophenol.

To 24.1 g out of the obtained solution, 5.0 g of 2-propanol was added, followed by addition of 0.29 g of platinum/carbon (carried amount of platinum: 3% by weight, water content: 61% by weight), and the solution was stirred at 40° C. under a hydrogen atmosphere (hydrogen partial pressure: 0.5 MPa) for 5 hours. The platinum/carbon was filtered from the reaction mixture, and the platinum/carbon was washed with 2-propanol. The filtrate and the washing solution were combined to obtain 24.8 g of a solution containing 4-(trifluoromethylsulfonyl)-2-aminophenol (content: 19.5% by weight). The obtained solution was concentrated to 19.6 g, and 5.0 g of heptane was added thereto at 40° C., and then the solution was cooled. Crystal precipitation was confirmed at 34° C., then the solution was cooled to 5° C., 15.0 g of heptane was further added at 5° C., and the mixture was kept at this temperature for 3 hours to precipitate crystals. The precipitated crystals were filtered, and washed with 12.5 g of a mixed solvent of 2-propanol/heptane=1/2, and the obtained crystals were dried under reduced pressure to obtain 4.8 g of 4-(trifluoromethylsulfonyl)-2-aminophenol (content: 98.7% by weight).

Example 4

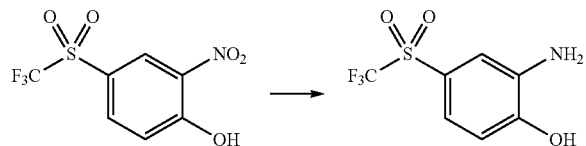 [SMILES: O=[N+]([O-])c1cc(S(=O)(=O)C(F)(F)F)ccc1O ; Nc1cc(S(=O)(=O)C(F)(F)F)ccc1O]

To a mixture of 10.00 g of 4-(trifluoromethylsulfonyl)-2-nitrophenol, 15.11 g of methanol, 2.12 g of toluene and 7.26 g of 2-ethylhexanoic acid, 21.6 mg of ammonium vanadate (V) was added followed by addition of 132.0 mg of platinum/carbon (carried amount of platinum: 3% by weight, water content: 55% by weight), and the solution was stirred at 40° C. under a hydrogen atmosphere (hydrogen partial pressure: 0.8 MPa) for 4 hours. The platinum/carbon was filtered from the reaction mixture, and the platinum/carbon was washed with methanol. The filtrate and the washing solution were combined to obtain 40.09 g (content: 21.94% by weight) of a solution containing 4-(trifluoromethylsulfonyl)-2-aminophenol.

Example 5

To a mixture of 24.99 g of 4-(trifluoromethylsulfanyl)phenol, 12.54 g of water, 12.49 g of octanoic acid ($CH_3$($CH_2$)$_6$COOH) and 0.84 g of sodium tungstate dihydrate, 52.07 g of 30% by weight of aqueous hydrogen peroxide was added dropwise at 75° C. over 17 hours, and the mixture was stirred for 20 hours. A 22% by weight of aqueous sodium sulfite solution was added dropwise to the reaction mixture, and the layers were separated to obtain 45.1 g (content: 57.9% by weight) of a solution containing 4-(trifluoromethylsulfonyl)phenol.

INDUSTRIAL APPLICABILITY

According to the present invention, 4-(trifluoromethylsulfonyl)phenol, 4-(trifluoromethylsulfonyl)-2-nitrophenol and 4-(trifluoromethylsulfonyl)-2-aminophenol which are useful as production intermediates of pharmaceuticals and agrochemicals can be produced.

The invention claimed is:

1. A method for producing a compound represented by formula (2):

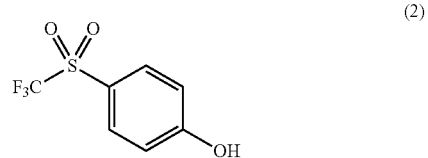 [SMILES: O=S(=O)(c1ccc(O)cc1)C(F)(F)F]

by oxidizing a compound represented by formula (1):

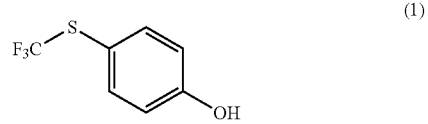 [SMILES: Oc1ccc(SC(F)(F)F)cc1]

with hydrogen peroxide in the presence of sodium tungstate and a saturated C8 carboxylic acid.

2. The method according to claim 1, wherein the amount of the saturated C8 carboxylic acid used is 0.5 to 2.0 times by weight of the compound (1).

3. A method for producing a compound represented by formula (3):

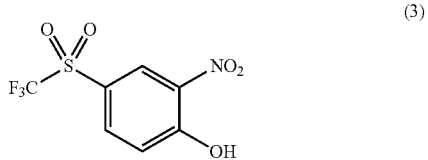 [SMILES: O=[N+]([O-])c1cc(S(=O)(=O)C(F)(F)F)ccc1O]

by oxidizing a compound represented by formula (1):

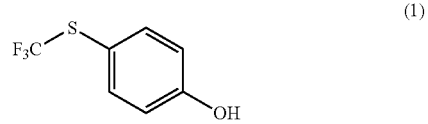 [SMILES: Oc1ccc(SC(F)(F)F)cc1]

with hydrogen peroxide in the presence of sodium tungstate and a saturated C8 carboxylic acid, then adding water to the resultant mixture, and separating the resultant solution to obtain a solution containing a compound represented by formula (2):

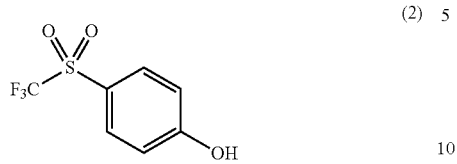
(2)

and by adding a nitrating agent to the solution containing a compound represented by formula (2).

4. The method according to claim 3, wherein the amount of the saturated C8 carboxylic acid used is 0.5 to 2.0 times by weight of the compound (1).

5. The method according to claim 1, wherein the saturated C8 carboxylic acid is 2-ethylhexanoic acid.

* * * * *